United States Patent [19]

Mariani et al.

[11] 4,402,970

[45] Sep. 6, 1983

[54] 1,7-DIHYDRO-PYRROLO[3,4-E][1,4]DIAZE-PIN-2(1H)-ONE DERIVATIVES

[75] Inventors: Luigi Mariani; Giorgio Tarzia, both of Milan, Italy

[73] Assignee: Gruppo Lepetit S.p.A., Milan, Italy

[21] Appl. No.: 381,272

[22] Filed: May 24, 1982

[30] Foreign Application Priority Data

Jul. 4, 1981 [GB] United Kingdom ............... 8117184

[51] Int. Cl.³ .................... A61K 31/55; C07D 487/04
[52] U.S. Cl. ........................... 424/274; 260/239.3 B;
548/340
[58] Field of Search ................. 260/239.3 B; 424/274

[56] References Cited

U.S. PATENT DOCUMENTS 3,257,382 6/1966 Bell .............................. 260/239.3 D
3,296,249 1/1967 Bell .............................. 260/239.3 D
4,022,766 5/1977 Fontanella et al. .......... 260/239.3 B

FOREIGN PATENT DOCUMENTS 826925 3/1975 Belgium ..................... 260/239.3 B

*Primary Examiner*—Robert T. Bond
*Attorney, Agent, or Firm*—William J. Stein; Raymond A. McDonald; Gary D. Street

[57] ABSTRACT

1,7-Dihydro-pyrrolo[3,4-e][1,4]diazepin-2(1H)-ones of the formula

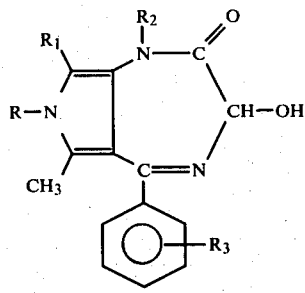

wherein R is lower alkyl, $R_1$ stands for hydrogen, methyl, ethyl or phenyl, $R_2$ is hydrogen or lower alkyl and $R_3$ is hydrogen, chloro, fluoro, bromo, trifluoromethyl or methoxy are described with anticonvulsant and anti-anxiety activity.

Also described is the process for preparing the above compounds and pharmaceutical preparations containing them.

13 Claims, No Drawings

1,7-DIHYDRO-PYRROLO[3,4-E][1,4]DIAZEPIN-2(1H)-ONE DERIVATIVES

The present invention refers to new pyrrolo-diazapine derivatives with anticonvulsant and anti-anxiety activity, to the process for preparing them, the intermediates for their synthesis, and to the pharmaceutical compositions containing the new compounds.

The new pyrrolodiazepine derivatives which are the first object of the present invention have the following general formula

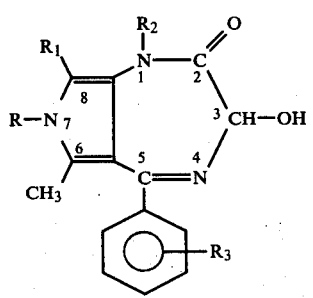

wherein R represents methyl, ethyl, propyl, 1-methylethyl, butyl, 1-methylpropyl, 2-methylpropyl, and 1,1-dimethylethyl, $R_1$ stands for hydrogen, methyl, ethyl, or phenyl, $R_2$ is hydrogen, methyl, ethyl, propyl, 1-methylethyl, butyl, 1-methylpropyl, 2-methylpropyl, and 1,1-dimethylethyl, and $R_3$ represents hydrogen, chloro, fluoro, bromo, trifluoromethyl and methoxy.

The new pyrrolodiazepines of the present invention are useful an anticonvulsant and anti-anxiety agents.

A preferred group of compounds comprises those compounds of formula I wherein R is methyl, $R_1$ is hydrogen, $R_2$ stands for hydrogen or methyl, and $R_3$ represents hydrogen, chloro, or fluoro.

A most preferred group comprises those compounds of formula I wherein R is methyl, $R_1$ is hydrogen, $R_2$ stands for hydrogen or methyl and $R_3$ represents hydrogen or chloro.

1,4-Diazepines fused on a pyrrole ring are described in Belgian Pat. No. 826,925. These compounds differ structurally from those of the present invention in the presence of a methylene group instead of a

group at the 3-position. Pharmacologically, the introduction of a hydroxy function at C-3 gives rise to a class of compounds unexpectedly more active as anticonvulsant and anti-anxiety agents than the most closely related prior-art compounds bearing a hydrogen atom at C-3, considerably less toxic, and surprisingly devoid of inducing activity.

The new compounds of the present invention are prepared starting from a N-(4-aroyl-5-methyl-(1H)pyrrol-3-yl) 2-iodoacetamide of formula II

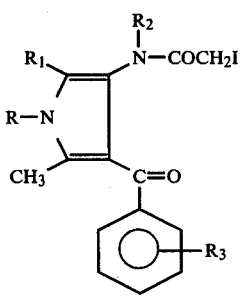

wherein R, $R_1$, $R_2$, and $R_3$ are as defined above, through a multi-step synthesis involving:

(a) reaction with hydroxylamine to give an N-(4-aroyl-5-methyl-(1H)pyrrol-3-yl) 2-hydroxylaminoacetamide III

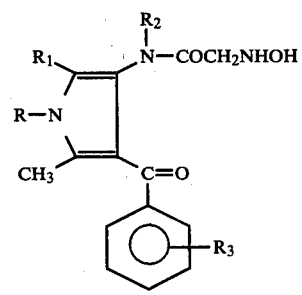

(b) cyclization of the obtained intermediate to yield an N-oxide of formula IV

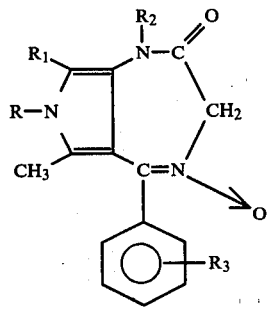

(c) rearrangement of this latter compound by treatment with acetic anhydride to a 3-acetoxy-pyrrolo[3,4-e][1,4]diazepine V

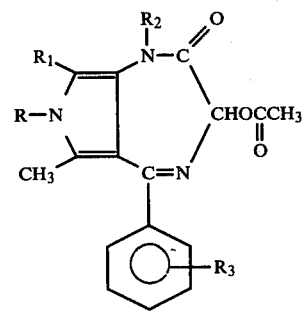

followed by (d) mild alkaline hydrolysis to the desired end compound of formula I.

In the actual practice the first step of the reaction scheme seen above, i.e. the reaction of the iodoacetamide derivative with hydroxylamine, is carried out by reacting the iodoacetamide derivative with an excess of hydroxylamine, preferably prepared in situ by adding an alkali metal hydroxide to an aqueous solution of hydroxylamine hydrochloride, in a lower alkanol.

When the reaction, which is followed by thin layer chromatography, is complete, the intermediate hydroxylaminoacetamide III is recovered according to conventional procedures which involve for instance evaporation of the reaction solvent and washing of the obtained residue, or strong dilution of the reaction mixture with salted water and recovery of the precipitate formed. If desired, the compound thus obtained, is purified by crystallization or it may be used as such in the second step of the reaction, the cyclization to N-oxide. Said cyclization passes through two steps. In the first one, the hydroxylaminoacetamide derivative III is converted into an intermediate diazepinium salt of formula VI

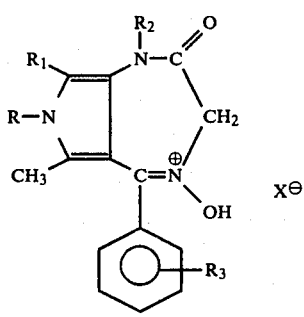

by heating, and preferably refluxing, a suspension of the hydroxylaminoacetamide derivative III in a lower alkanol in the presence of a strong acid HX. Acids which may conveniently be employed in this step can be hydrochloric, sulfuric, methanesulfonic and the like acids. In the second step, the intermediate diazepinium salt, recovered by crystallization from the alcoholic solvent, is transformed, with or withoug previous characterization, into the N-oxide IV by treatment with aqueous bases such as alkali metal hydroxides or carbonates in aqueous solutions. Rearrangement of the N-oxide IV with acetic anhydride smoothly takes place by suspending the N-oxide IV in acetic anhydride at room temperature. In general, however the reaction mixture is heated for a few minutes in order to complete the reaction. The resulting 3-acetoxy derivative V, which is recovered by crystallization from the reaction solvent, is then submitted to mild alkaline hydrolysis yielding the desired end compound of formula I. This hydrolytic step may simply be carried out by heating the 3-acetoxy derivative V with an equimolar amount of an alkali metal hydroxide in aqueous alcoholic solvents. Furthermore, when a compound of formula I is desired wherein $R_2$ is a lower alkyl group, it may be prepared also starting from a compound II wherein $R_2$ is hydrogen, and submitting either the 3-acetoxy intermediate V or the N-oxide IV, obtained by following the process described above, to common alkylation procedures before further processing these intermediates as seen above.

In the former case the reaction is conveniently carried out by contacting the 3-acetoxy intermediate with an alkyl halide $R_2X$ wherein $R_2$ is a lower alkyl group as defined above and X stands for chloro, bromo or iodo, in the presence of a strong base such as an alkali metal amide, hydride, hydroxide or alkoxide, and once the alkylation reaction is complete, by adding water to bring out the deacetylation. In the latter case, i.e. when the alkylation reaction is carried out on the N-oxides IV, it is more conveniently carried out in aqueous alkali. The starting iodoacetamide derivatives of formula II are easily prepared from the corresponding chloroacetamide derivatives VII

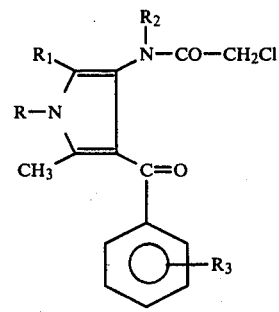

through reaction with an alkali metal iodide in ethanol or acetone according to the Finkelstein reaction. In their turn the chloroacetamide derivatives VII are prepared through reaction of chloroacetic acid chloride with a 3-aroyl-4-aminopyrrole compound of formula VIII

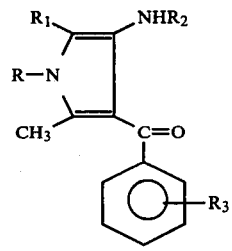

wherein R, $R_1$, $R_2$, and $R_3$ have the same meanings as above. These latter compounds can be obtained by alkylation at the pyrrole nitrogen atom, and optionally at the amine nitrogen atom also, of the corresponding 3-aroyl-4-aminopyrrole derivative VIII wherein R and $R_2$ are hydrogen prepared by reacting an α-aminonitrile of formula

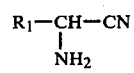

with a β-diketone of formula

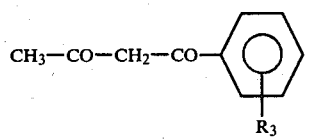

according to conventional procedures.

A further specific object of the present invention is the intermediates of formula IV and V obtained in the above synthetic pathway.

The novel compounds of the present invention as well as the intermediates of formula IV and V possess anticonvulsant and anti-anxiety activity.

To evaluate the anticonvulsant activity the compounds of the present invention have been submitted to the antipentylenetetrazole bioassay in mice. The experiments have been carried out by following essentially the methodology described by Berger in J. Pharm. Exptl. Ther. 104, 468, (1952). More particularly, a fatal dose of pentylenetetrazole (140 mg/kg s.c.) was administered to groups of ten mice each, treated, 30 minutes before the administration of the convulsant agent, with a selected dose of the potential anticonvulsant compound. One of these groups, the "control" group, did not receive the anticonvulsant but only the convulsant agent. Since the animals of the control group died within 30 minutes, the effectiveness of the compounds tested, at each dose tested, was expressed as the number of animals of the group which were still alive two hours after the administration of pentylenetetrazole, out of the total number of animals of the group (10).

By testing each compound at different doses, the corresponding $ED_{50}$, i.e. the dose at which 50% of the treated animals are protected, was calculated. The results obtained in these experiments are reported in the following Table A.

TABLE A

| Compound of example No. | $ED_{50}$ mg/kg os |
|---|---|
| 9 | 7.5 |
| 10 | 7.5 |
| 11 | 5 |

The same test was carried out also with 3,7-dihydro-6,7-dimethyl-5-phenyl-pyrrol[3,4-e][1,4]diazepin-2(1H)-one (IX)

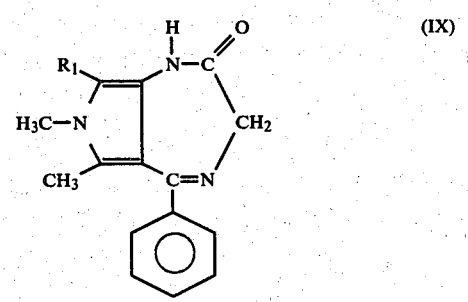

(IX)

This compound, which is the most active compound of the class of pyrrolodiazepines described in Belgian Pat. No. 826,925, showed to be at least twice less active than the compounds of the present invention since its $ED_{50}$ calculated in the same way as for the compounds of the present invention, is 15 mg/kg/os.

The anti-anxiety activity of the compounds of the present invention was first shown by submitting the compounds to the "benzodiazepine receptors" test both in vitro and in vivo. It was recently discovered in fact that there exist specific binding sites for benzodiazepines in the central nervous system which act in mediating the anxiolytic properties of benzodiazepines, and it was demonstrated (see for instance S. Lippa et al., Pharmacol. Biochem. & Behaviour, Vol. 9, 853–856 (1978) and H. Möler and T. Okada, Brit. J. Psychiat., 133, 261–68 (1978)) that the ability of a substance to displace $^3$H-Diazepam from its specific rat brain receptors, both in vitro and in vivo, is significantly correlated with its anxiolytic properties.

The in vitro experiments were carried out by following the method described by H. Möler and T. Okada in Life Sciences Vol. 20, 2101–2110 (1977) while those in vivo were carried out according to the procedures illustrated by S. Lippa et al. in Pharmacol. Biochem. & Behaviour, Vol. 9, pp. 853–856 (1978).

The results obtained in these tests with some representative compounds of the present invention and with 3,7-dihydro-6,7-dimethyl-5-phenylpyrrolo[3,4-e][1,4]diazepin-2-(1H)-one, the compound known from Belgian Pat. No. 826,925, are summarized in the following Table B.

TABLE B

| Compound of example No. | "in vitro" Ki | "in vivo" % inhibition at 1 mg/kg/os |
|---|---|---|
| 5 | $45.9 \times 10^{-9}$ | −45 |
| 11 | $2.82 \times 10^{-9}$ | −54 |
| 3,7-dihydro-6,7-dimethyl-5-phenylpyrrolo-[3,4-e][1,4]diazepin-2(1H)-one | $97 \times 10^{-9}$ | −33 |

The anxiolytic activity of the compounds of the present invention was then confirmed by the results obtained in other experiments in animals. More particularly the ability of the compounds of the present invention to increase punished responding in a conflict situation, a procedure with high validity for predicting the anxiolytic effect of drugs, was assessed by testing these compounds in rats according to the method described by I. Geller and J. Seifter in Psychopharmacologia 1, 482, (1960). Briefly, in this test, rats are trained to press a lever in order to get a food reward, and each rat exhibits a characteristic and rather stable rate of lever pressing. During an audible signal of a few minutes duration that is occasionally presented, each press of the lever will provide a food reward but will be accompanied by a brief electric shock. A situation of conflict between the rat's desire for food and his fear of the shock soon develops. The rate of lever pressing during the punished period, in the absence of drug treatment, is highly reduced, and each rat develops a characteristic response pattern during the conflict period.

The experiments carried out showed that the compounds of the present invention, when administered by the oral route to these trained animals, were able to remarkably increase rat's responses during the conflict period at doses which did not influence the characteristic rate of lever pressing during the non-conflict portion.

Another behavioural test which confirmed the anti-anxiety properties of the compounds of the present invention was the so-called "taming effect" test carried out on naturally vicious and aggressive monkeys.

The "taming effect" on monkeys is one of the most meaningful and reliable parameters with which the anti-anxiety properties of a compound can be investigated. A drug supposed to be an anti-anxiety but not a CNS-depressant agent must in fact relieve the animals from anxiety but let them react normally to the external stimuli, i.e. it must alter the animals' naturally hostile and aggressive behaviour at doses at which CNS-depressant side-effects do not occur. A true "taming effect", as an indication of the anti-anxiety properties of a compound not ascribable to CNS-depression, is reached when the animals become docile and friendly so as to accept food from the observer's hand. In this test, the compounds of examples 10 and 11 of the present invention, at the oral dose of 1 mg/kg, displayed a true "taming effect" in at least 50% of the treated animals. Furthermore, the compounds of the present invention, unlike the prior-art compounds, showed to be devoid of inducing activity.

More particularly while the 3,7-dihydro-6,7-dimethyl-5-phenylpyrrolo[3,4-e][1,4]diazepin-2(1H)-one described in Belgian Pat. No. 826,925 potentiated the "sleeping time" induced by hexobarbital in rats starting from 1 mg/kg p.o., the compounds of examples 5 and 11 of the present invention, tested in the same conditions, did not show this potentiating effect even at higher doses. This is considered as an indication of the absence of inducing activity. These favorable pharmacological properties of the compounds of the present invention are accompanied by a low toxicity, lower than that of the prior-art compounds. As an example, while the acute oral toxicity of the prior-art 3,7-dihydro-6,7-dimethyl-5-phenylpyrrolo[3,4-e][1,4]diazepin-2(1H)-one in mice is about 500 mg/kg, that of the compound of example 5 of the present invention is comprised between 600 and 700 mg/kg and that of the compound of example 11 is higher than 20,000 mg/kg.

In view of the above, the use of the compounds of the present invention as anticonvulsant and anti-anxiety agents, is a further specific object of the present invention.

With the term "use" it is intended to refer to all industrially applicable aspects and acts of said use, including the embodiment of the novel compounds into pharmaceutical compositions.

Suitable pharmaceutical compositions contain the novel compounds in admixture or conjunction with organic or inorganic, solid or liquid pharmaceutical excipients and may be employed for enteral and parenteral administration. Suitable excipients are substances that do not react with the new compounds such as for instance, water, gelatin, lactose, starches, magnesium stearate, talcum, vegetable oils, benzyl alcohol, polyalkyleneglycols, or other known medicinal excipients. The new compounds may be administered by various routes: orally, intramuscularly or intravenously, for example. For oral administration the substances are compounded in such forms, as tablets, dispersible powders, capsules, granules, syrups, elixirs and solutions. For intravenous or intramuscular administration the active ingredients are embodied into injectable dosage forms. Such compositions are formulated as known in the art.

The dosage regimen for the compounds of the present invention in accord with anticonvulsant, anti-anxiety treatment will depend upon a variety of factors including the particular compound used, the route of administration, and the type of treatment applied for. Good results can be obtained however by administering the compounds of the present invention at a daily dosage range comprised between about 0.05 and about 3 mg/kg preferably in divided doses. It is however clear that a daily dosage beyond the above indicated range may also be employed depending on the individual conditions of the subject to be treated.

Accordingly the present invention provides a therapeutic composition containing from about 2.5 to about 150 mg of one of the compounds of the invention as the active ingredient together with a pharmaceutically acceptable carrier.

Following are illustrative pharmaceutical formulations which may be employed in practicing the present invention:

|  | Per Tablet |
|---|---|
| Preparation of a tablet formulation: | |
| 5-(2-chlorophenyl-1,7-dihydro-3-hydroxy-1,6,7-trimethylpyrrolo[3,4-e][1,4]diazepin-2(1H)-one | 25 mg |
| starch | 25 mg |
| Aerosil ® V 200 | 1.25 mg |
| magnesium stearate | 1 mg |
| lactose | q.s. to 180 mg |
| Preparation of a capsule formulation | |
| 5-(2-chlorophenyl)-1,7-dihydro-3-hydroxy-6,7-dimethylpyrrolo[3,4-e][1,4-]diazepin-2(1H)-one | 20 mg |
| starch | 20 mg |
| magnesium stearate | 1 mg |
| lactose | q.s. to 180 mg |

The following examples describe in details some of the compounds of the invention and illustrate the process for preparing them without limiting the scope of the present invention.

EXAMPLE 1

N-(4-benzoyl-1,5-dimethyl (1H)pyrrol-3-yl)-2-hydroxylaminoacetamide

Sodium hydroxide (64 g) was added to a solution of hydroxylamine hydrochloride (111 g) in water (370 ml) and the obtained solution was diluted with ethanol (3500 ml). N-(4-benzoyl-1,5-dimethyl (1H)pyrrol-3-yl)-2-iodoacetamide (124.5 g) was then added and the obtained suspension was stirred under nitrogen stream for about 48 hours. The reaction mixture was filtered in order to remove the salts and the filtrate was concentrated to dryness at the pump. The residue was washed with a small amount of water and crystallized from ethyl acetate yielding 82.5 g of the compound of the title. M.p. 140°–42° C.

EXAMPLE 2

1,2,3,7-tetrahydro-4-hydroxy-6,7-dimethyl-2-oxo-5-phenyl-pyrrolo[3,4-e][1,4]diazepinium chloride The compound of example 1 (79.4 g) was suspended in isopropanol containing 2.1% of HCl (3700 ml) and refluxed for 2 hours with stirring. The reaction mixture was then cooled to 0° C. and a first crop (61 g) of the compound of the title which crystallized out was recovered by filtration. A second crop (9 g) was obtained by concentrating the mother liquors to a small volume. M.p. 220°–223° C. with decomposition.

EXAMPLE 3

1,7-Dihydro-6,7-dimethyl-5-phenyl-pyrrole[3,5-e][1,4]diazepin-2(1H)-one-4-oxide

The compound of example 2 (140 g) was dissolved in water (1400 ml), the obtained solution was cleared by filtration and brought to pH 9 by the addition of Na$_2$CO$_3$ with stirring. NaCl (400 g) was then added to the suspension, and stirring was continued for further 60 minutes. The compound of the title which precipitated was then recovered by filtration (113 g). M.p. 255°–258° C.

EXAMPLE 4

3-Acetoxy-1,7-dihydro-6,7-dimethyl-5-phenyl-pyrrolo[3,4-e][1,4]diazepin-2(1H)-one The compound obtained in Example 3 was suspended in acetic anhydride (500 ml) and the temperature of the reaction raised to 75° C. in a few minutes. The reaction mixture was heated to 85° C. for 20 minutes with stirring then it was cooled to 0° C. and the crystalline precipitate was recovered yielding 117 g of the compound of the title. M.p. 255°-56° C.

EXAMPLE 5

1,7-Dihydro-3-hydroxy-6,7-dimethyl-5-phenyl-pyrrolo[3,4-e][1,4]diazepin-2(1H)-one To a suspension of the compound of Example 4 (40 g) in ethanol (2000 ml), cooled to 5° C., 1N NaOH (128 ml) was added with stirring. After 10 minutes the reaction mixture was cooled to about 4° C. and allowed to stand at this temperature for one night. Then $CO_2$ was gradually added to the solution to lower the pH to about 8. Ethanol was evaporated off at the pump and the obtained residue was washed first with water and then with methanol, and crystallized from ethanol yielding 30 g of the compound of the title. M.p. 243° C. with decomposition.

EXAMPLE 6

1,7-Dihydro-3-hydroxy-1,6,7-trimethyl-5-phenyl-pyrrolo[3,4-e][1,4]diazepin-2(1H)-one The compound of Example 4 (25 g) was gradually added to a suspension of sodium amide prepared from sodium (2.2 g) in liquid ammonia (900 ml), and the mixture was stirred for 30 minutes. Then methyl iodide (40 ml) was dripped into the mixture and stirring was continued until complete evaporation of ammonia. The reaction mixture was then diluted with water and the oily suspension was extracted with ethyl acetate. The ethyl acetate solution was washed with water, dried, and concentrated to dryness. The residue was finally crystallized from ethanol yielding 10.5 g of the compound of the title. M.p. 179°-81° C.

EXAMPLE 7

N-[4-(2-chlorobenzoyl)-1,5-dimethyl(1H)pyrrol-3-yl)]2-hydroxylaminoacetamide

The compound of the title was prepared by following essentially the procedures described in example 1 but prolonging the reaction time to 72 hours. The compound of the title was then recovered by diluting the reaction mixture with water (5 times the initial volume) containing NaCl (5.5 kg) and filtering the precipitate which crystallized out. M.p. 166°-68° C. with decomposition.

EXAMPLE 8

5-(2-Chlorophenyl-1,7-dihydro-6,7-dimethyl-pyrrolo[3,4-e][1,4]diazepin(1H)-one-4-oxide Methansulfonic acid (38 ml) was added to a suspension of the compound of the preceding example (137 g) in ethanol (3000 ml) and the reaction mixture was refluxed for 11 hours. The solvent was then evaporated off at the pump and the residue was taken up with water. The solution was alkalinized with $Na_2CO_3$, salted with NaCl and extracted with ethyl acetate. The organic extract was dried over $Na_2SO_4$ and concentrated to dryness yielding a raw residue which was washed with ether and crystallized from ethanol/ether yielding 115 g of the compound of the title. M.p. 220° C. with decomposition.

EXAMPLE 9

5-(2-chlorophenyl)-3-acetoxy-1,7-dihydro-6,7-dimethylpyrrolo[3,4-e][1,4]diazepin-2-(1H)-one The compound of the title was prepared by following the procedure described in example 4 but starting from the compound of the foregoing example. M.p. 244°-46° C. Yield 59.5%.

EXAMPLE 10

5-(2-Chlorophenyl)-1,7-dihydro-3-hydroxy-6,7-dimethylpyrrolo[3,4-e][1,4-diazepin-2(1H)-one The compound of the title was prepared by following essentially the procedure described in Example 5 but starting from the compound of Example 9. M.p. 201°-203° C.

EXAMPLE 11

5-(2-Chlorophenyl)-1,7-dihydro-3-hydroxy-1,6,7-trimethylpyrrolo[3,4-e][1,4]diazepin-2(1H)-one By following the procedure described in Example 6 but starting from the compound of Example 9 the compound of the title was obtained. M.p. 178°-80° C.

EXAMPLE 12

5-(2-chlorophenyl)-1,7-dihydro-6,7-dimethylpyrrolo[3,4-e][1,4]diazepin-2(1H)-one-4-oxide A suspension of N-[4-(2-chlorobenzoyl)-1,5-dimethyl(1H)-pyrrol-3-yl]2-hydroxylaminoacetamide (130 g) in a solution of sulfuric acid (250 ml) in water (2400 ml) was heated to 80° C. for 1 hour. The reaction mixture was cooled to 20° C., cleared by filtration, diluted with water (1500 ml) and filtered again. The acidic solution was then cautiously alkalinized by the addition of $Na_2CO_3$ and extracted with chloroform. By concentrating the organic extracts to dryness under vacuum at room temperature, 80 g of the compound of the title were recovered.

EXAMPLE 13

5-(2-chlorophenyl-1,7-dihydro-1,6,7-trimethylpyrrolo[3,4-e][1,4]diazepin-2(1H)-one-4-oxide A solution of NaOH (27 g) in water (4700 ml) was added with stirring to 5-(2-chlorophenyl)-1,7-dihydro-6,7-dimethylpyrrolo[3,4-e][1,4]diazepin-2(1H)-one-4-oxide (165 g) finely suspended in ethanol (940 ml). Then, dimethylsulfate (54.7 ml) was added during 10 minutes keeping the temperature at about 20° C. The reaction mixture was stirred at this temperature for 2 hours, then the insoluble was separated by under vacuum filtration. The clear solution was salted with NaCl and extracted with chloroform. The organic extract was dried over $Na_2SO_4$, and concentrated to dryness under vacuum at 25°-30° C. The residue was washed with ethyl ether yielding 135 g of the compound of the title. M.p. 198°-200° C. (from isopropanol).

EXAMPLE 14

3-Acetoxy-5-(2-chlorophenyl)-1,7-dihydro-1,6,7-trimethylpyrrolo[3,4-e][1,4]diazepin-2(1H)-one The compound of Example 13 (160 g) was suspended in acetic anhydride (660 ml) and the reaction flask was dipped in a water-bath at 55° C. After stirring for 15 minutes the reaction mixture was concentrated to dryness under vacuum, and the obtained residue was taken up with boiling ethanol and treated with charcoal.

By concentrating to a volume of 600 ml and cooling, the compound of the title (103 g) crystallized out. M.p. 202°-4° C.

EXAMPLE 15

5-(2-chlorophenyl)-1,7-dihydro-3-hydroxy-1,6,7-trimethylpyrrolo [3,4-e][1,4]diazepin-2(1H)-one 1N NaOH (557 ml) was added to a suspension of 3-acetoxy-5-(2-chlorophenyl)-1,7-dihydro-1,6,7-trimethylpyrrolo[3,4-e][1,4]diazepin-2(1H)-one (200 g) in ethanol (1500 ml) keeping the temperature between 0 and 5° C. After stirring at 5° C. for 1 hour the suspension was gradually poured into a solution of NaCl (2 kg) in water (7500 ml), and the precipitate which formed was recovered by under vacuum filtration and washed first with water, and then with cold methanol yielding 160 g of the compound of the title. Further 17 g were obtained by extracting the filtrate with ethyl acetate and evaporating off the extracting solvent. M.p. 182°-83° C. (from ethyl acetate).

Preparation of the starting iodoacetamide derivative II

EXAMPLE 16

N-(4-benzoyl-1,5-dimethyl(1H)pyrrol-3-yl)-2-iodoacetamide (a) 4-amino-3-benzoyl-2-methylpyrrole:

Aminoacetonitrile (0.04 mole) and benzoyl acetone (0.04 mole) were refluxed for four hours in 30 ml of anhydrous benzene in the presence of 100 mg of p-toluensulfonic acid. After cooling the reaction mixture was filtered and the solvent was evaporated off to give an oily residue which was dissolved in an ethanol solution containing sodium ethoxide (0.041 mole). The mixture was allowed to stand for 12 hours at room temperature and the solid precipitate which forms was recovered by filtration.

(b) N-(4-benzoyl-5-methyl(1H)pyrrol-3-yl)2-chloroacetamide:

4-Amino-3-benzoyl-2-methylpyrrole (0.019 mole) was dissolved in water (40 ml) and the solution was treated with charcoal (0.1 g) and filtered. Chloroacetylchloride (0.067 mole) and aqueous NaOH (58.1 ml, 20% w/v) were added separately and simultaneously during 1 hour to the stirred solution. The reaction mixture was maintained under an inert atmosphere and at room temperature for 1.5 hour. The compound of the title which spontaneously crystallized out of the reaction mixture, was collected by filtration.

(c) N-(4-benzoyl-1,5-dimethyl(1H)pyrrol-3-yl)2-chloroacetamide:

N-(4-benzoyl-5-methyl(1H)-pyrrol-3-yl)2-chloroacetamide (0.019 mole) was dissolved in butan-2-one (60 ml) and $K_2CO_3$ (4.5 g) and dimethylsulphate (0.037 mole) were added to the obtained solution. The reaction mixture was maintained at the reflux temperature for 5 hours and at room temperature overnight. An inert atmosphere was maintained throughout the process. The inorganic salts were filtered off and the clear solution was evaporated under vacuum to yield a residue which upon crystallization from methanol gave the compound of the title.

(d) N-(4-benzoyl-1,5-dimethyl(1H)pyrrol-3-yl)2-iodoacetamide:

N-(4-benzoyl-1,5-dimethyl(1H)pyrrol-3-yl)2-chloroacetamide (0.741 mole) and potassium iodide (1.62 mole) were refluxed in ethanol (3400 ml) for 5 hours with stirring. The reaction mixture was then cooled, the inorganic salts were filtered off and the solvent was evaporated under vacuum. The obtained residue was purified by washing first with water and then with cold ethanol. M.p. 135°-137° C. Yield 87%.

EXAMPLE 17

N-(4-(2-chlorobenzoyl)-1,5-dimethyl(1H)pyrrol-3-yl)2-iodoacetamide

The compound of the title was prepared by following the procedures described in the foregoing example but starting from (2-chlorobenzoyl)acetone instead of benzoylacetone. M.p. 155°-57° C.

We claim:

1. A pyrrolo[3,4-e][1,4]diazepin of the formula

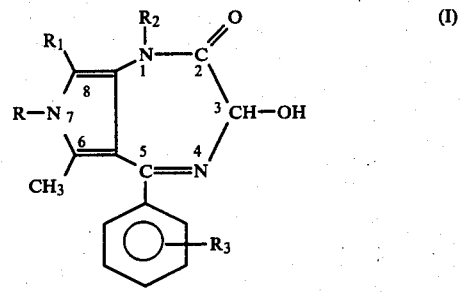

wherein R represents methyl, ethyl, propyl, 1-methylethyl, butyl, 1-methylpropyl, 2-methylpropyl, and 1,1-dimethylethyl, $R_1$ stands for hydrogen, methyl, ethyl, or phenyl, $R_2$ is hydrogen, methyl, ethyl, propyl, 1-methylethyl, butyl, 1-methylpropyl, 2-methylpropyl, and 1,1-dimethylethyl, and $R_3$ represents hydrogen, chloro, fluoro, bromo, trifluoromethyl and methoxy.

2. A compound as in claim 1 wherein R is methyl, $R_1$ is hydrogen, $R_2$ stands for hydrogen or methyl, and $R_3$ represents hydrogen, chloro or fluoro.

3. A compound as in claim 2 wherein R is methyl, $R_1$ is hydrogen, $R_2$ stands for hydrogen or methyl, and $R_3$ is hydrogen or chloro.

4. An intermediate compound of formula IV

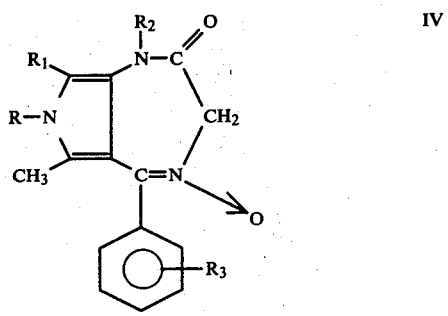

or of formula V

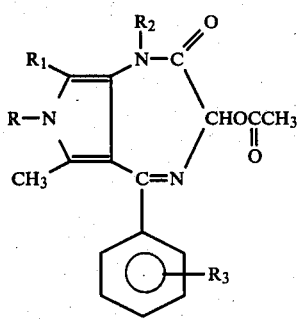

wherein R represents methyl, ethyl, propyl, 1-methylethyl, butyl, 1-methylpropyl, 2-methylpropyl, and 1,1-dimethylethyl, $R_1$ stands for hydrogen, methyl, ethyl or phenyl, $R_2$ is hydrogen, methyl, ethyl, propyl, 1-methylethyl, butyl, 1-methylpropyl, 2-methylpropyl, and 1,1-dimethylethyl, and $R_3$ represents hydrogen, chloro, fluoro, bromo, trifluoromethyl, and methoxy.

5. A compound as in claim 4 wherein R is methyl, $R_1$ is hydrogen, $R_2$ stands for hydrogen or methyl, and $R_3$ represents hydrogen, chloro or fluoro.

6. A compound as in claim 5 wherein R is methyl, $R_1$ is hydrogen, $R_2$ stands for hydrogen or methyl, and $R_3$ is hydrogen or chloro.

7. An anti-convulsant or anti-anxiety pharmaceutical composition consisting essentially of an inert pharmaceutical carrier and an effective anti-convulsant or anti-anxiety amount of a compound of claim 1.

8. An anti-convulsant or anti-anxiety pharmaceutical composition consisting essentially of an inert pharmaceutical carrier and an effective anti-convulsant or anti-anxiety amount of a compound of claim 4.

9. A pharmaceutical composition as in claim 7 which contains from about 2.5 to about 150 mg. of a compound of claim 1 together with a pharmaceutically acceptable carrier.

10. A pharmaceutical composition as in claim 8 which contains from about 2.5 to about 150 mg. of a compound of claim 4 together with a pharmaceutically acceptable carrier.

11. A compound according to claim 1 which is 5-(2-chlorophenyl)-1,7-dihydro-3-hydroxy-6,7-dimethylpyrrolo[3,4-e][1,4]diazepin-2(1H)-one.

12. A compound according to claim 1 which is 5-(2-chlorophenyl)-1,7-dihydro-3-hydroxy-1,6,7-trimethylpyrrolo[3,4-e][1,4]diazepin-2(1H)-one.

13. A compound according to claim 4 which is 5-(2-chlorophenyl)-3-acetoxy-1,7-dihydro-6,7-dimethylpyrrolo[3,4-e][1,4]diazepin-2(1H)-one.

* * * * *